(12) United States Patent
Mitschke et al.

(10) Patent No.: US 6,932,506 B2
(45) Date of Patent: Aug. 23, 2005

(54) REGISTRATION METHOD AND APPARATUS FOR NAVIGATION-GUIDED MEDICAL INTERVENTIONS, WITHOUT THE USE OF PATIENT-ASSOCIATED MARKERS

(75) Inventors: Matthias Mitschke, Nuremberg (DE); Dieter Ritter, Fuerth (DE)

(73) Assignee: Siemens Aktiengesellschaft (DE)

( * ) Notice: Subject to any disclaimer, the term of this patent is extended or adjusted under 35 U.S.C. 154(b) by 1 day.

(21) Appl. No.: 10/383,942

(22) Filed: Mar. 7, 2003

(65) Prior Publication Data

US 2003/0219102 A1 Nov. 27, 2003

(30) Foreign Application Priority Data

Mar. 8, 2002 (DE) ......................................... 102 10 287

(51) Int. Cl.[7] .............................................. G01D 18/00
(52) U.S. Cl. ...................... 378/207; 378/162; 250/252.1
(58) Field of Search ......................... 378/162, 18, 207, 378/163, 208, 157, 205; 600/426, 427; 250/252.1

(56) References Cited

U.S. PATENT DOCUMENTS

| | | | | |
|---|---|---|---|---|
| 5,224,147 A | * | 6/1993 | Collin et al. ................ | 378/162 |
| 6,379,043 B1 | * | 4/2002 | Zylka et al. ................ | 378/207 |
| 6,382,835 B2 | * | 5/2002 | Graumann et al. ......... | 378/198 |
| 6,490,475 B1 | * | 12/2002 | Seeley et al. ............... | 600/426 |
| 6,491,430 B1 | * | 12/2002 | Seissler ...................... | 378/207 |
| 6,533,455 B2 | * | 3/2003 | Graumann et al. ......... | 378/205 |

FOREIGN PATENT DOCUMENTS

DE  OS 199 17 8673  11/2000

* cited by examiner

Primary Examiner—Edward J. Glick
Assistant Examiner—Irakli Kiknadze
(74) Attorney, Agent, or Firm—Schiff Hardin LLP

(57) ABSTRACT

A registration method and an apparatus for navigation-guided interventions employing an X-ray device and a position acquisition system and avoid the use of patient-associated markers. By means of a defined arrangement of a carrying arm proceeding from a support mount at the X-ray device and a defined arrangement of an X-ray calibration phantom at the carrying arm, the coordinate transformation between a coordinate system allocated to the support mount and a coordinate system allocated to the X-ray calibration phantom is known. On the basis of the acquisition and evaluation of 2D projections of the X-ray calibration phantom with the X-ray device, a coordinate transformation between the coordinate system allocated to the support mount and a coordinate system allocated to a measurement volume of the X-ray device is produced. By arranging a device detectable by the position acquisition system at the support mount, a coordinate transformation between the coordinate system allocated to the measurement volume and a coordinate system allocated to the calibration phantom is determined for the navigation.

20 Claims, 3 Drawing Sheets

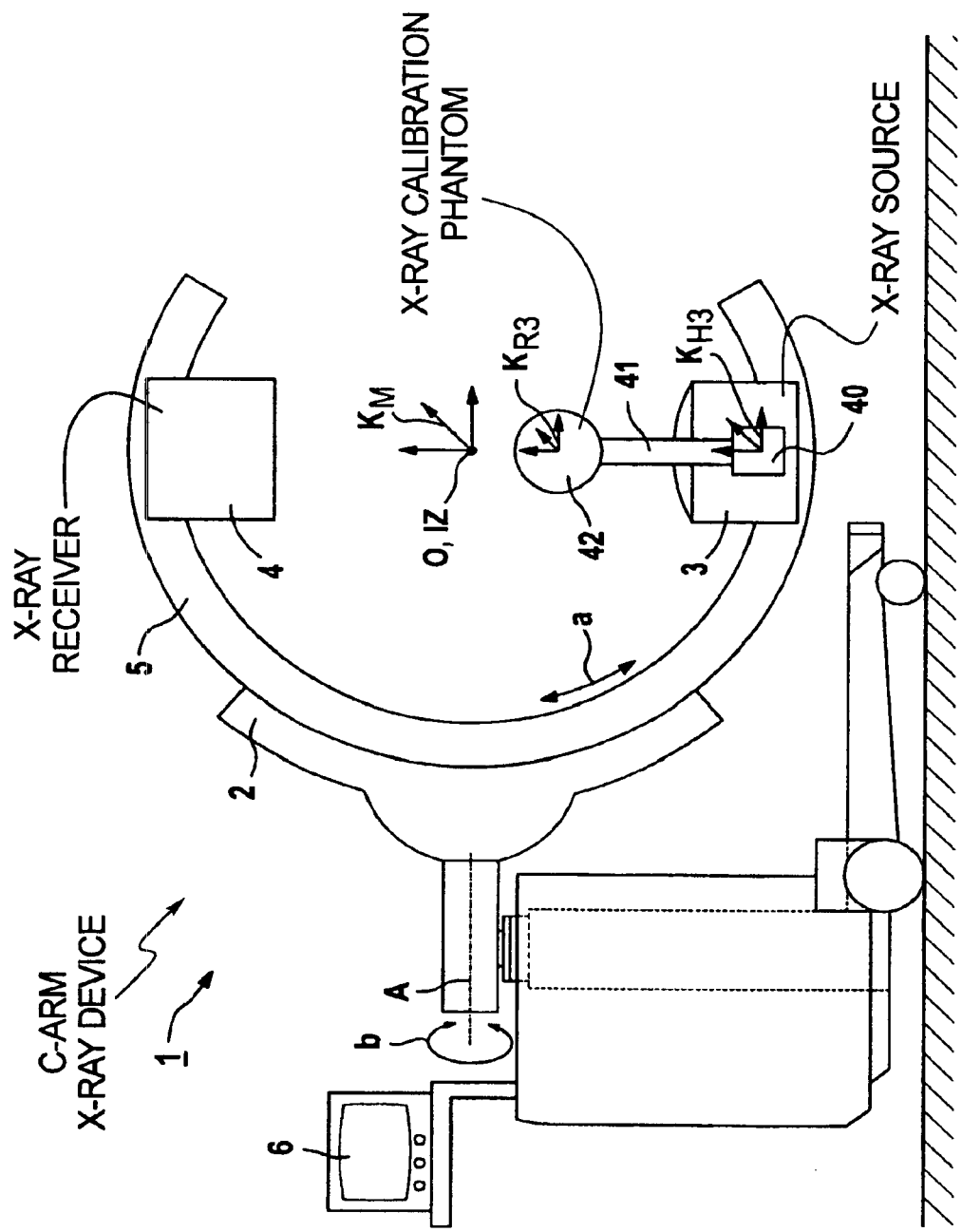

REGISTRATION METHOD AND APPARATUS FOR NAVIGATION-GUIDED MEDICAL INTERVENTIONS, WITHOUT THE USE OF PATIENT-ASSOCIATED MARKERS

BACKGROUND OF THE INVENTION

1. Field of the Invention

The invention is directed to a registration method for navigation-guided medical interventions of the type wherein a coordinate transformation that is employed for navigation is determined between a coordinate system of a position acquisition system and a measurement volume of an X-ray device. The invention is also directed to an apparatus for the implementation of the method. The method and apparatus of the invention do not require patient-associated markers.

2. Description of the Prior Art

Navigation is increasingly being used for supporting medical interventions at living subjects, this being understood as the guidance of a medical instrument relative to a subject or relative to a tissue region of subject being treated, that is supported by means of optical image information. An image of the instrument is mixed into a 2D or 3D image of the subject acquired with the X-ray device. In this way, an operator can guide an instrument that has at least partially penetrated into the subject so that its tip is no longer directly visible, for example due to the penetration into body tissue, relative to the tissue region of the subject on the basis of the image information without a risk of unintentionally harming the subject.

In order to enable such a navigation-guided intervention, i.e. in order to be able to mix an image of the instrument into image information of a subject in a manner that is accurate as to position and orientation, it is necessary to produce a mathematical relationship in the form of a coordinate transformation between a coordinate system of the image information of the subject or a coordinate system of the reconstructed volume of the subject and a coordinate system with respect which the positions of the instrument are indicated. To this end, artificial markers are sometimes arranged at the subject or anatomical markers, for example distinct bone structures, are defined. The anatomical or artificial markers (patient-associated markers) must be clearly visible in the image information of the subject registered with the X-ray device and must be easily accessible at the subject. For example, the artificial markers are secured to the skin surface of the subject order to be able to undertake a registration, which is understood to mean the determination of the spatial transformation rule between the coordinate system wherein the positions of the instrument to be navigated are defined and the coordinate system of the image information or of the reconstructed volume of the subject. The markers usually must be individually approached with the instrument in a specified sequence in order to be able to determine the coordinate transformation between the two coordinate systems. In extremely precise medical interventions, the markers are secured to the body of the subject so as to be immobile. The attachment of a stereotactic frame to the head of a patient and the attachment of markers in bones or at the spinal column of a patient are as examples. The attachment of the markers partly ensues in a separate operation since the markers must already be applied before a pre-operative imaging that is frequently employed for navigation.

The attachment and registration of the markers, accordingly, is a relatively unpleasant procedure for a patient and is also relatively time-consuming for an operator in preparing a navigation-guided intervention.

SUMMARY OF THE INVENTION

An object of the present invention is to provide a simplified method for markerless determination of the transformation rule in a navigation-guided medical intervention as well as an apparatus for the implementation of the method.

This object is inventively achieved by making a series of 2D projections from different projection directions of an X-ray calibration phantom on a carrying arm is secured, via a support mount, in a defined way to the X-ray device for alignment relative to the X-ray device. A coordinate transformation between a coordinate system allocated to the X-ray calibration phantom and a coordinate system allocated to a measurement volume of the X-ray device is determined from the 2D projections. Since the coordinate transformation between the coordinate system allocated to the X-ray calibration phantom and a coordinate system allocated to the support mount is known, due to the defined arrangement of the carrying arm at the support mount and the defined arrangement of the X-ray calibration phantom at the carrying arm, the coordinate transformation between the coordinate system allocated to the support mount and the coordinate system allocated to the measurement volume of the X-ray device can be unproblemmatically determined. When, after the determination of this coordinate transformation, a marker plate provided with markers is finally arranged, for example, at the support mount of the X-ray device, the marker plate being detectable by a position acquisition system, then coordinates of the coordinate system allocated to the measurement volume can be transformed into coordinates of a coordinate system allocated to the position acquisition system and vice versa. For medical applications, for example, coordinates of a medical instrument acquired with respect to the coordinate system of the position acquisition system can be transformed into coordinates of the coordinate system of the measurement volume. Mixing of images of the instrument into images of a subject produced with the X-ray device thus is possible without registration, i.e. without employing markers to be attached to a subject.

In a version of the invention, the X-ray device is a C-arm X-ray device, the C-arm of which is preferably isocentrically adjustable. The C-arm X-ray device has a support for the C-arm in which the C-arm is adjustable along its circumference, and the support mount for the calibration phantom is arranged at the support. When the carrying arm provided with the X-ray calibration phantom is secured to the support mount arranged at the support, then, given an adjustment of the C-arm around its orbital axis, the phantom can remain at the support mount during the entire acquisition of the series of 2D projections from different projection directions. In another version of the invention the support mount is arranged at the X-ray receiver of the X-ray device that moves relative to the X-ray calibration phantom during the acquisition of the series of 2D projections. The phantom is releasably connected to the carrying arm. An adjustable stand, preferably placeable on the floor, to which the X-ray calibration phantom can be secured is provided. The stand is preferably adjustable in five degrees of freedom. After arranging the carrying arm provided with the X-ray calibration phantom in a defined position at the X-ray receiver, the X-ray calibration phantom is arranged on the stand without changing its position and that the connection between the X-ray calibration phantom and the carrying arm is released. The X-ray calibration phantom is then only held at the stand. For acquiring the series of 2D projections, finally, the carrying arm is removed from the support mount of the X-ray device, and the series of 2D projections of the X-ray calibration phantom, now arranged only at the stand, is acquired from different projection directions.

In a further embodiment, a first series of 2D projections of an X-ray calibration phantom is acquired with the X-ray device and projection matrices for the X-ray device are determined therefrom. Subsequently, at least one further 2D projection in at least one defined position of the carrying device for the X-ray source and an X-ray receiver is acquired from the same or from some other X-ray calibration phantom that is secured in a defined way to a carrying arm securable via a support mount to the X-ray device, for alignment relative to the X-ray device. A second projection matrix is determined from this (at least one) further 2D projection. The coordinate transformation between the coordinate system allocated to the support mount and the coordinate system allocated to the X-ray calibration phantom is known due to the defined arrangement of the carrying arm at the support mount and the defined arrangement of the X-ray calibration phantom at the carrying arm. Therefore, the coordinate transformation between the coordinate system allocated to the support mount and a coordinate system allocated to a measurement volume of the X-ray device can be determined on the basis of a first projection matrix that is allocated to the defined position of the carrying device and that was determined during the course of determining the first projection matrix and on the basis of the second projection matrix, which is allocated to the defined position of the carrying device. As mentioned above, a marker plate that, for example, can be detected by a position acquisition system, is arranged at the support of the X-ray device after the determination of this coordinate transformation, then images of medical instruments can be mixed without registration into the images of a subject generated with the X-ray device.

In this embodiment as well, the X-ray device can be a C-arm X-ray device with a C-arm that is preferably isocentrically adjustable, and the support mount can be arranged at the X-ray source of the X-ray device.

DESCRIPTION OF THE DRAWINGS

FIG. 3 is a side view of a C-arm X-ray device constructed and operating in accordance with the invention, with a support mount arranged at the X-ray source, to which a carrying arm provided with an X-ray calibration phantom is secured.

DESCRIPTION OF THE PREFERRED EMBODIMENTS

Figure 1:
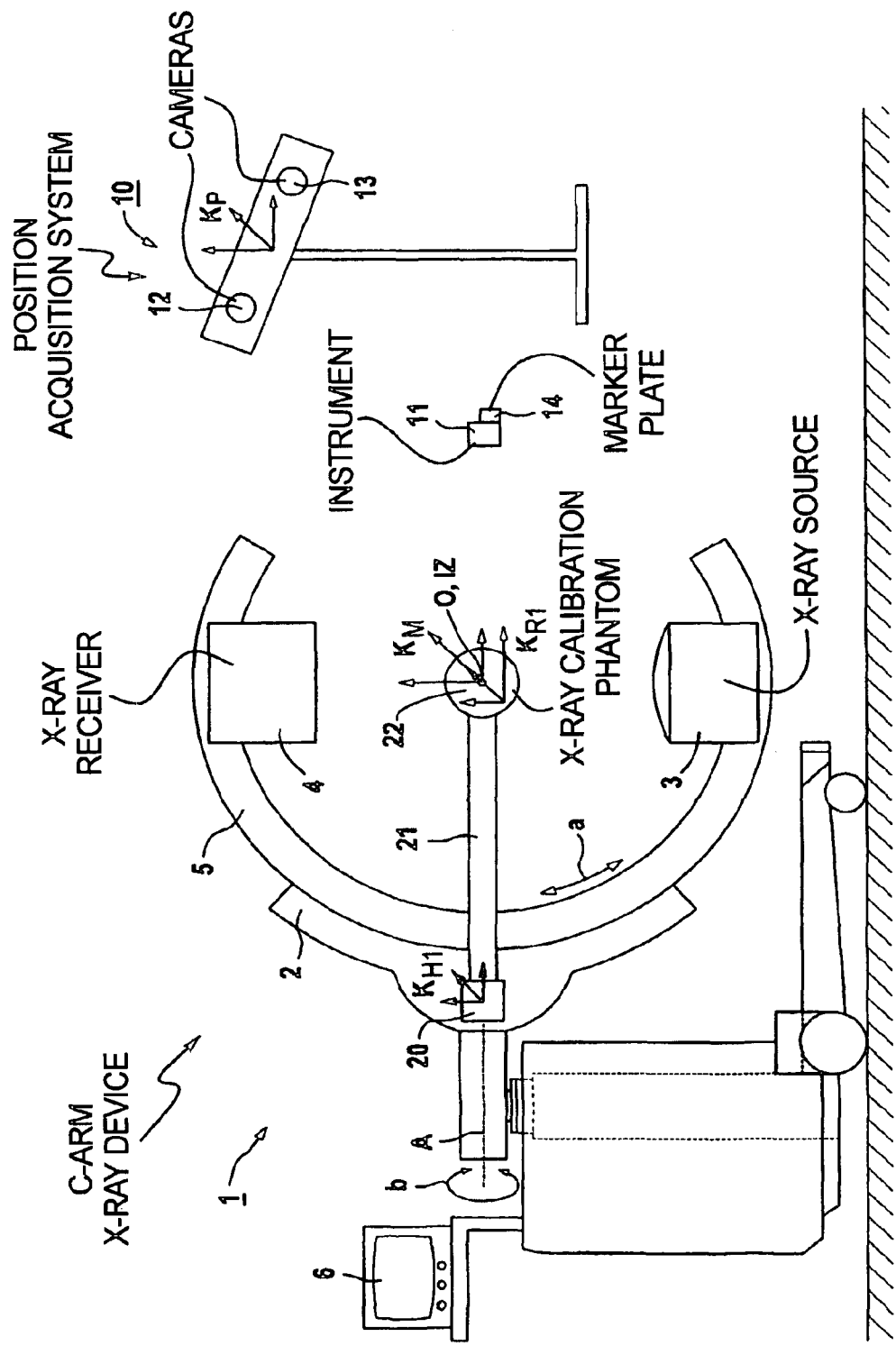
FIG. 1 is a side view of a C-arm X-ray device constructed with a support mount arranged at a bearing part of the C-arm X-ray device and to which a carrying arm provided with an X-ray calibration phantom is secured.

A C-arm X-ray device 1 shown in FIG. 1 has components arranged in a known manner, with the differences in accordance with the invention described below. The C-arm X-ray device has a support 2 at which a C-arm 5 provided with an X-ray source 3 and an X-ray receiver 4 is seated. In the exemplary embodiment, the C-arm 5 is isocentrically adjustable (see the double arrow 'a') along its circumference around its isocenter IZ and its orbital axis O. Together with the support 2, the C-arm 5 is also isocentrically pivotable around its angulation axis A in the directions of the double arrow 'b'.

2D and 3D images of subjects, for example patients, can be acquired with the C-arm X-ray device 1 and presented on a display device 6. The devices required for this purpose, particularly an image computer, are implemented in a known way and are therefore not shown in FIG. 1 and need not be explicitly described.

Particularly for medical applications, navigation-guided interventions at a patient (not shown) are to be implemented with the C-arm X-ray device 1. For this reason, it is necessary to determine a coordinate transformation between a coordinate system $K_M$ that is allocated to a measurement of the C-arm X-ray device 1, and has its origin in the isocenter IZ of the C-arm X-ray device 1 in the exemplary embodiment, and a coordinate system $K_P$ allocated to a position acquisition system 10 (schematically shown in FIG. 1) wherein the coordinates of an instrument 11 to be navigated relative to a patient are defined.

To this end, a support mount 20 to which a coordinate system $K_{H1}$ is allocated is arranged at the support 2 of the C-arm X-ray device 1. A carrying arm 21 that is removable from the support mount 20 is secured to the support mount 20. An X-ray calibration phantom 22 is secured to the carrying arm 21, with a coordinate system $K_{R1}$ being allocated to the X-ray calibration phantom 22. The carrying arm 21 is arranged in a defined manner at the support mount 20 and the X-ray calibration phantom 22 is arranged in a defined manner at the carrying arm 21 so that the coordinate transformation between the coordinate system $K_{H1}$ allocated to the support mount 20 and the coordinate system $K_{R1}$ allocated to the X-ray calibration phantom 22 is known on the basis of the known dimensions of the carrying arm 21.

For determining the coordinate transformation between the coordinate system $K_{R1}$ allocated to the X-ray calibration phantom 22 and the coordinate system $K_M$ allocated to the measurement volume of the C-arm X-ray device 1, a series of 2D projections of the X-ray calibration phantom 22 is acquired from different projection directions by movement of the C-arm 5 around its orbital axis O. The X-ray calibration phantom 22 is arranged at the carrying arm 21 so that it is penetrated by an X-ray beam proceeding from the X-ray source 3 to the X-ray receiver 4. The coordinate transformation between the coordinate system $K_{R1}$ allocated to the X-ray calibration phantom 22 and the coordinate system $K_M$ allocated to the measurement volume of the C-arm X-ray device 1 is determined from the acquired series of 2D projections of the X-ray calibration phantom 22. To this end, moreover, the X-ray calibration phantom 22 has X-ray-positive marks in a known way that are imaged in the 2D projections. The orientation of the X-ray-positive marks in the coordinate system $K_{R1}$ allocated to the X-ray calibration phantom 22 is thereby known.

Since, thus, the coordinate transformation between the coordinate system $K_{H1}$ allocated to the support mount 20 and the coordinate system $K_{R1}$ allocated to the X-ray calibration phantom 22, and the coordinate transformation between the coordinate system $K_{R1}$ allocated to the X-ray calibration phantom 22 and the coordinate system $K_M$ allocated to the measurement volume of the C-arm X-ray device 1, are known, the coordinate transformation between the coordinate system $K_{H1}$ allocated to the support mount 20 and the coordinate system $K_M$ allocated to the measurement volume can also be determined in a simple way. This latter transformation, for example, is stored in a memory (not shown in FIG. 1) of the C-arm X-ray device 1.

When the C-arm X-ray device 1 is to be utilized for navigation-guided interventions at a patient, the carrying arm 21 provided with the X-ray calibration phantom 22 is removed from the support mount 20, and a marker plate (not shown in FIG. 1 but well known) that is provided with markers is arranged in a defined manner at the support mount 20 of the C-arm X-ray device 1 thus the coordinate system $K_{H1}$ allocated to the support mount 2 is also allocated to the marker plate in the exemplary embodiment.

The coordinate transformation between the coordinate system $K_{H1}$ allocated to the marker plate 20 and the coordinate system $K_P$ allocated to the position acquisition system can be determined from camera images acquired with cameras 12, 13 of the position acquisition system 10 wherein the marker plate is imaged, so that—overall—the coordinate transformation between the coordinate system $K_M$ allocated to the C-arm X-ray device 1 and the coordinate system $K_P$ allocated to the position acquisition system can be determined, for example with a computer (not shown in FIG. 1). This computer can be allocated to the position acquisition system 10 or can be the image computer (likewise not shown in FIG. 1) of the C-arm X-ray device 1. Camera images are acquired of the instrument 11, provided with a marker plate 14 having markers during the course of a navigation-guided intervention. The positions of the instrument 11 with respect to the coordinate system $K_P$ allocated to the position acquisition system 10 thus can be determined on the basis of the camera images, and these can be can be transformed into coordinates of the coordinate system $K_M$ of the measurement volume on the basis of the identified coordinate transformation between the coordinate system $K_P$ allocated to the position acquisition system 10 and the coordinate system $K_M$ allocated to the measurement volume. For guidance of the instrument 11 relative to a patient, images of the instrument 11 can be mixed into X-ray images of the patient acquired with the C-arm X-ray device 1.

Figure 2:
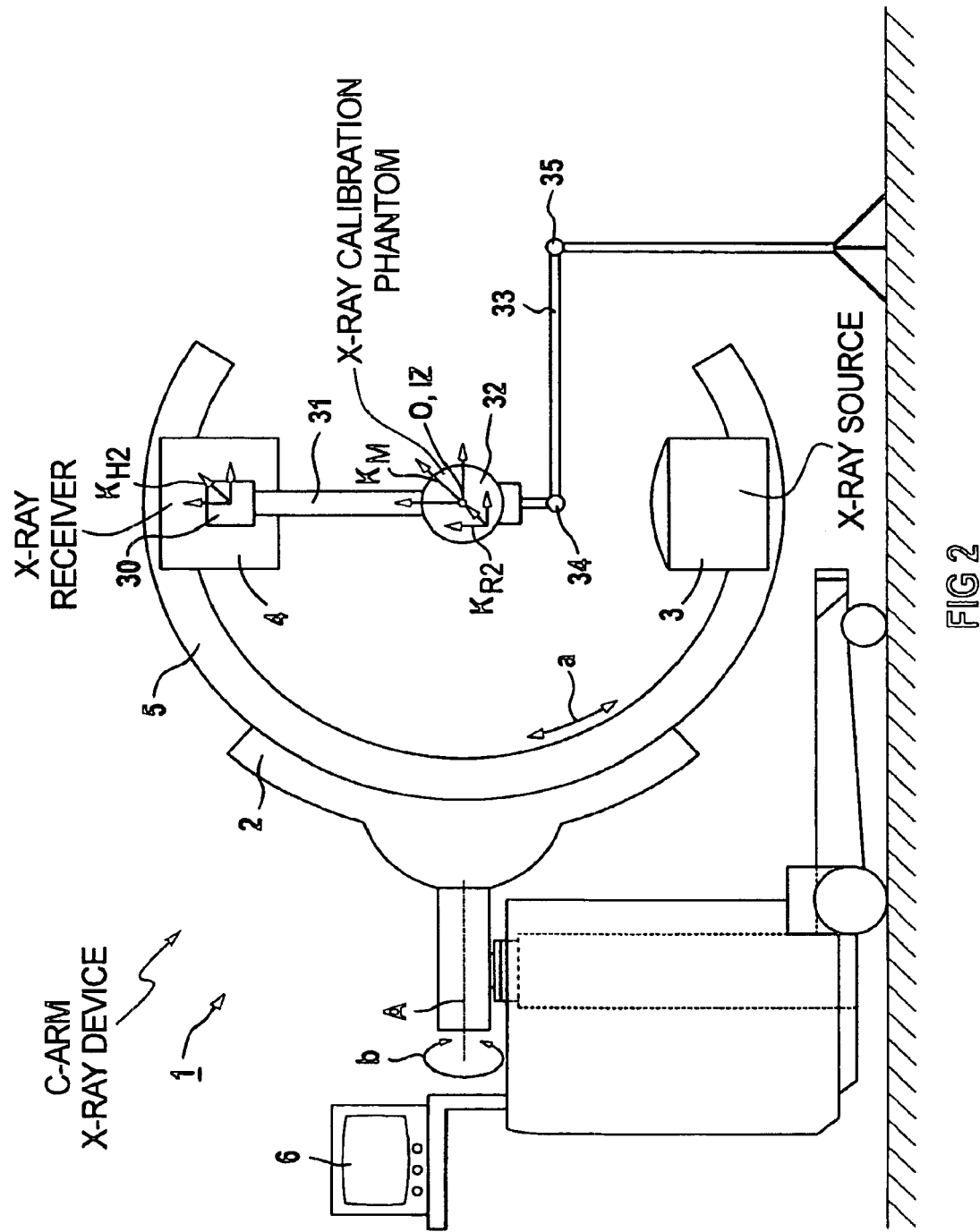
FIG. 2 is a side view of a C-arm X-ray device constructed and operating in accordance with the invention, with a support mount arranged at the X-ray reception device at which a carrying arm provided with an X-ray calibration phantom is arranged.

FIG. 2 illustrates a second possibility for determining a coordinate transformation between a coordinate system allocated to a measurement volume of a C-arm X-ray device and a coordinate system allocated to the C-arm X-ray device itself without the use of markers in the registration. The C-arm X-ray device shown in FIG. 2 essentially corresponds to the C-arm X-ray device shown in FIG. 1, so the components of the C-arm X-ray device are provided with the same reference characters. Differing from the C-arm X-ray device 1 shown in FIG. 1, the C-arm X-ray device 1 shown in FIG. 2 has a support mount 30 arranged at the radiation receiver 4. The support mount 30 has a coordinate system $K_{H2}$ allocated to it. A carrying arm 31 at which an X-ray calibration phantom 32 is arranged in a defined way is arranged at the support mount 30 in a defined way. The X-ray calibration phantom 32 is releasably attached to the carrying arm 31. Like the X-ray calibration phantom 22, the X-ray calibration phantom 32 has X-ray-positive marks (not shown). The orientation of these marks relative to a coordinate system $K_{R2}$ allocated to the X-ray calibration phantom 32 is known. Due to the defined arrangements of the carrying arm 31 at the support mount 30 and the X-ray calibration phantom 32 at the carrying arm 31, as well as due to the known dimensions of the carrying arm 31, the coordinate transformation between the coordinate system $K_{H2}$ allocated to the support mount 30 and the coordinate system $K_{R2}$ allocated to the X-ray calibration phantom 32 is known.

As can be seen from FIG. 2, the X-ray calibration phantom 32 is arranged at a stand 33 standing on the floor in addition to being arranged at the carrying arm 31. The arrangement of the X-ray calibration phantom 32 at the stand 33 does not ensue until after the fastening of the carrying arm 31 provided with the X-ray calibration phantom 32 to the support mount 30. In the present exemplary embodiment, the stand 33 is (in a way not shown in detail) height-adjustable, and is adjustable around ball-and-socket joints 34, 35 for this purpose. For acquiring 2D projections of the X-ray calibration phantom 32 from different projection directions, the carrying arm 31 is released from the X-ray calibration phantom 32 and thus from the support mount 30, but the orientation of the X-ray calibration phantom 32 does not change relative to the support mount 30 nor relative to the C-arm X-ray device 1, so that the transformation rule between the coordinate system $K_{H2}$ allocated to the support mount 30 and the coordinate system $K_{R2}$ allocated to the X-ray calibration phantom 32, which is known due to the defined arrangement of the X-ray calibration phantom 32 at the carrying arm 31 and of the carrying arm 31 at the support mount 30, is preserved.

For determining the coordinate transformation between the coordinate system $K_{R2}$ allocated to the X-ray calibration phantom 32 and the coordinate system $K_M$ allocated to the measurement volume of the C-arm X-ray device 1, a series of 2D projections of the X-ray calibration phantom 32 from different projection directions is acquired–after the removal of the carrying arm 31–by movement of the C-arm 5 around its orbital axis. The coordinate transformation between the coordinate system $K_{R2}$ allocated to the X-ray calibration phantom 32 and the coordinate system $K_M$ allocated to the measurement of the C-arm X-ray device 1 is then determined from the acquired series of 2D projections of the X-ray calibration phantom 32.

Since, thus, the coordinate transformation between the coordinate system $K_{H2}$ allocated to the support mount 30 and the coordinate system $K_{R2}$ allocated to the X-ray calibration phantom 32 and the coordinate transformation between the coordinate system $K_{R2}$ allocated to the X-ray calibration phantom 32 and the coordinate system $K_M$ allocated to the measurement volume of the C-arm X-ray device 1 are known, the coordinate transformation between the coordinate system $K_{H2}$ allocated to the support mount 30 and the coordinate system $K_M$ allocated to the measurement volume can also be determined in a simple way. This latter transformation can be stored in a memory (not shown in FIG. 2) of the C-arm X-ray device 1.

A marker plate detectable by the position acquisition system 10 is arranged at the support mount 30 in a defined manner so that—as in the exemplary embodiment shown in FIG. 1—the coordinate system $K_{H2}$ allocated to the support mount 30 can also be allocated to the marker plate. A transformation rule between the coordinate system $K_{M\ allocated}$ to the measurement volume and a coordinate system allocated to a position acquisition system thus can be determined. As a result, the pre-conditions are established for mixing images of an instrument into X-ray images of, for example, a patient acquired with the C-arm X-ray device 1.

FIG. 3 illustrates a third possibility for determining a coordinate transformation between a coordinate system allocated to a C-arm X-ray device and a coordinate system allocated to the measurement volume of the C-arm X-ray device. The C-arm X-ray device shown in FIG. 3 corresponds to the C-arm X-ray device 1 shown in FIG. 1 and FIG. 2, so that the components of the C-arm X-ray device shown in FIG. 3 are provided with the same reference characters as the components of the C-arm X-ray device 1 shown in FIGS. 1 and 2. The C-arm X-ray device 1 shown in FIG. 3 differs from the C-arm X-ray devices 1 shown in FIGS. 1 and 2 by virtue of a support mount 40, to which a coordinate system $K_{H3}$ is allocated, being arranged at the X-ray source 3. A carrying arm 41 is arranged at the support mount 40 in a defined way and an X-ray calibration phantom 42 is arranged at the carrying arm 41 in a defined way. Like the X-ray calibration phantoms 22 and 32, the X-ray calibration phantom 42 has X-ray-positive marks whose orientation relative to a coordinate system $K_{R3}$ allocated to the X-ray calibration phantom 42 is known. Due to the defined arrangements of the carrying arm 41 at the support mount 40 and the X-ray calibration phantom 42 at the carrying arm 41 as well as due to the known dimensions of the carrying arm 41, the coordinate transformation between the coordinate system $K_{H3}$ allocated to the support mount 40 and the coordinate system $K_{R3}$ allocated to the X-ray calibration phantom 42 is known.

For determining the coordinate transformation between the coordinate system $K_{H3}$ allocated to the support mount 40 and the coordinate system $K_M$ allocated to the measurement volume, and before the carrying arm 41 provided with the X-ray calibration phantom 42 is arranged at the support mount 40, the X-ray calibration phantom 42 or some other X-ray calibration phantom is arranged relative to the C-arm X-ray device 1 independently of the carrying arm 41, for example on any kind of substrate, so that an X-ray beam emanating from the X-ray source 3 can penetrate the X-ray calibration phantom. The X-ray calibration phantom 42 is employed in the exemplary embodiment. A first series of 2D projections of the X-ray calibration phantom 42 is acquired from different projection directions by moving the C-arm 5 around the orbital axis O, for example along its circumference. First projection matrices for the C-arm X-ray device 1 are determined therefrom and deposited in a memory of the C-arm X-ray device 1. Subsequently, the carrying arm 41 provided with the X-ray calibration phantom 42 is arranged at the support mount 40, as shown in FIG. 3. A 2D projection of the X-ray calibration phantom 42 is now acquired at an arbitrarily selectable but defined position of the C-arm 5. The only requirement is that C-arm this C-arm position must be a position of the C-arm 5 that this assumed in the acquisition of a 2D projection of the first series of 2D projections. A second projection matrix belonging to this position of the C-arm 5 is determined from this 2D projection. Based on the known coordinate transformation between the coordinate system $K_{H3}$ allocated to the support mount 40 and the coordinate system $K_{R3}$ allocated to the X-ray calibration phantom 42 as well as based on a first projection matrix that is allocated to the defined position of the C-arm 5, determined during the course of determining the first projection matrices, and based on the second projection matrix that is allocated to the defined position of the C-arm 5, the coordinate transformation between the coordinate system $K_{H3}$ allocated to the support mount 40 and the coordinate system $K_M$ allocated to the measurement of the C-arm X-ray device 1 is calculated. The calculation thereby ensues on the basis of the following equation:

$$P_1 = P_2 * T(K_{H3}; K_{R3}) * T(K_{H3}; K_M),$$

wherein $P_1$ is the first projection matrix that is allocated to the defined position of the C-arm 5, $P_2$ is the second projection matrix that is allocated to the defined position of the C-arm 5, and $T(K_{H3}; K_{R3})$ is the known transformation rule between the coordinate systems $K_{H3}$ and $K_{R3}$. $T(K_{H3}; K_M)$ is the sought transformation rule between the coordinate systems $K_{H3}$ and $K_M$.

By resolution of the projection matrix $P_1$ into an extrinsic component and an intrinsic component as well as by resolution of the projection matrix that proceeds from a matrix multiplication of the projection matrix $P_2$ by the transformation rule $T(K_{H3}; K_{R3})$ into an intrinsic component and extrinsic component, the transformation rule $T(K_{H3}; K_M)$ can be composed of a rotary component and a translational component that are formed from the extrinsic components of the resolutions of the projection matrices. Accordingly, the transformation rule between the coordinate system $K_{H3}$ allocated to the support mount 40 and the coordinate system $K_M$ allocated to the measurement volume can be determined in this way, so that the preconditions are established for being able to mix images of an instrument into X-ray images of, for example, a patient acquired with the C-arm X-ray device 1, with the assistance of a position acquisition system, for example the position acquisition system 10 of FIG. 1.

In the exemplary embodiment shown in FIG. 3, moreover, second projection matrices can be acquired in a number of defined positions of the C-arm 5 on the basis of 2D projections of the X-ray calibration phantom 42 acquired at these position in order to determine the transformation rule between the coordinate system $K_{H3}$ allocated to the support mount 40 and the coordinate system $K_M$ allocated to the measurement volume. It must be noted, however, that the second projection geometries of the C-arm X-ray device 1 may possibly be modified by the weight of the carrying arm 41 and of the X-ray calibration phantom 42. This would then require an additional calibration of the C-arm X-ray device 1 with the carrying arm and the X-ray calibration phantom 42 arranged thereat.

In the exemplary embodiments, the C-arm 5 is moved around its orbital axis O in order to acquire 2D projections of the X-ray calibration phantom. The C-arm 5 alternatively can be moved around its angulation axis A for acquiring 2D projections.

Further, the X-ray device need not necessarily be a C-arm X-ray device.

The arrangements of the support mounts 20, 30 and 40 as described in the exemplary embodiments are examples. In the exemplary embodiment shown in FIG. 1, for example, the support mount 20 alternatively can be arranged in a component of the C-arm X-ray device 1 that is immobile during the acquisition of the 2D projections. In the case of the exemplary embodiment shown in FIG. 2, further, the support mount 30 alternatively can be arranged at the X-ray source 3 or at the C-arm 5. The situation is the same in the exemplary embodiment shown in FIG. 3.

Although modifications and changes may be suggested by those skilled in the art, it is the intention of the inventors to embody within the patent warranted hereon all changes and modifications as reasonably and properly come within the scope of their contribution to the art.

We claim as our invention:

1. A registration method for navigation-guided medical interventions at a patient, with no patient-associated markers, comprising the steps of:

disposing a support mount relative to an imaging X-ray device, having a measurement volume, and fastening a carrying arm to said support mount;

fastening an X-ray calibration phantom at a defined location of said carrying arm at which said X-ray calibration phantom is penetrated by an X-ray beam emitted by an X-ray source of said X-ray device, thus producing a known coordinate transformation between a coordinate system allocated to said support mount and a coordinate system allocated to said X-ray calibration phantom;

acquiring a series of 2D projections of said X-ray calibration phantom from different projection directions using said X-ray device; and determining, based on said series of 2D projections, a coordinate transformation between the coordinate system allocated to the measurement volume and the coordinate system allocated to the calibration phantom, and from said coordinate transformation and said known coordinate transformation, determining a coordinate transformation between the coordinate system allocated to the support mount and a coordinate system allocated to said measurement volume.

2. A method as claimed in claim 1 comprising employing a C-arm X-ray device as said imaging X-ray device.

3. A method as claimed in claim 2 wherein said C-arm X-ray device has a C-arm with a circumference, and a support for said C-arm wherein said C-arm is movable along said circumference, and wherein the step of disposing said support mount relative to said imaging X-ray device comprises attaching said support mount at said support for said C-arm.

4. A method as claimed in claim 1 wherein said imaging X-ray device has a radiation receiver, and wherein the step of disposing said support mount relative to said imaging X-ray device comprises attaching said support mount at said radiation receiver.

5. A method as claimed in claim 4 comprising the additional steps of providing an adjustable stand and supporting said X-ray calibration phantom on said adjustable stand in addition to fastening said X-ray calibration phantom at said defined location of said carrying arm.

6. A method as claimed in claim 5 wherein the step of fastening said X-ray calibration phantom at a defined location of said carrying arm comprises releasably fastening said X-ray calibration phantom at said defined location of said carrying arm, and releasing said X-ray calibration phantom from said carrying arm prior to acquiring said series of 2D projections, and acquiring said series of 2D projections with said X-ray calibration phantom supported only by said adjustable stand, with said X-ray calibration phantom remaining at said defined location.

7. A method as claimed in claim 1 comprising the additional steps of:

attaching markers to said imaging X-ray device;

detecting respective positions of said markers with a position acquisition system having a position acquisition system coordinate system associated therewith; and transforming coordinates of said coordinate system allocated to said measurement volume into coordinates of said coordinate system allocated to said position acquisition system.

8. A method as claimed in claim 7 wherein the step of attaching a plurality of markers to said imaging X-ray device comprises attaching said plurality of markers to said support mount.

9. A method as claimed in claim 7 comprising the additional steps of:

obtaining an image of a subject disposed in said measurement volume using said imaging X-ray device;

introducing an instrument into said subject in said measurement volume; and using said transformation between said coordinate system allocated to the measurement volume and said coordinate system allocated to the position acquisition system, mixing an image of said instrument into said image of said subject.

10. A registration method for a navigation-guided medical intervention, with no patient-associated markers, comprising the steps of:

disposing an X-ray calibration phantom relative to an imaging X-ray device having an X-ray source, said imaging X-ray device having a measurement volume;

acquiring a first series of 2D projections of said X-ray calibration phantom with said imaging X-ray device from different projection directions;

determining first projection matrices for said imaging X-ray device from said first series of 2D projections;

disposing a support mount relative to said imaging X-ray device and fastening a carrying arm to said support mount;

fastening an X-ray calibration phantom at a defined location of said carrying arm at which said X-ray calibration phantom fastened to said carrying arm is penetrated by X-rays emitted from said X-ray source of said imaging X-ray device, thereby producing a known coordinate transformation between a coordinate system allocated to said support mount and a coordinate system allocated to said X-ray calibration phantom;

acquiring at least one further 2D projection of said X-ray calibration phantom fastened to said carrying arm in at least one defined position of a carrying device of said imaging X-ray device for said X-ray source and a radiation receiver which receives the X-rays emitted by said X-ray source;

determining a second projection matrix belonging to said defined position of said carrying device from said at least one further 2D projection; and from a first projection matrix of said first projection matrices and from said second projection matrix, and from said known coordinate transformation, determining a coordinate transformation between the coordinate system allocated to the support mount and a coordinate system allocated to said measurement volume.

11. A method as claimed in claim 10 comprising employing a C-arm X-ray device as said imaging X-ray device.

12. A method as claimed in claim 10 wherein the step of disposing a support mount relative to said imaging X-ray device comprises attaching said support mount to said X-ray source of said imaging X-ray device.

13. A method as claimed in claim 10 comprising the additional steps of:

attaching markers to said imaging X-ray device;

detecting respective positions of said markers with a position acquisition system having a position acquisition system coordinate system associated therewith; and transforming coordinates of said coordinate system allocated to said measurement volume into coordinates of said coordinate system allocated to said position acquisition system.

14. A method as claimed in claim 13 wherein the step of attaching a plurality of markers to said imaging X-ray device comprises attaching said plurality of markers to said support mount.

15. A method as claimed in claim 13 comprising the additional steps of:

obtaining an image of a subject disposed in said measurement volume using said imaging X-ray device;

introducing an instrument into said subject in said measurement volume; and using said transformation between said coordinate system allocated to the measurement volume and said coordinate system allocated to the position acquisition system, mixing an image of said instrument into said image of said subject.

16. A registration apparatus for navigation-guided medical interventions, with no patient-associated markers, comprising:

an imaging X-ray device having an X-ray source which emits an X-ray beam;

a support mount attached to said imaging X-ray device;

a carrying arm attached to said support mount; and an X-ray calibration phantom attached to said carrying arm at a defined location at which said X-ray calibration phantom is penetrated by and attenuates said X-ray beam from said X-ray source to produce a visible contribution in an X-ray image obtained with said imaging X-ray device.

17. An apparatus as claimed in claim 10 wherein said imaging X-ray device is a C-arm X-ray device.

18. An apparatus as claimed in claim 16 further comprising a plurality of markers attached to said imaging X-ray device and a position acquisition system for identifying respective positions of said markers in a coordinate system allocated to said position acquisition system.

19. An apparatus as claimed in claim 18 wherein said plurality of markers is attached to said support mount.

20. An apparatus as claimed in claim 18 wherein said imaging X-ray device is adapted to obtain an image of a subject disposed in said X-ray beam, and wherein an instrument is introduced into said subject, said apparatus further comprising a display on which said image of said subject is presented with an image of said instrument mixed therein, dependent on the respective positions of said markers.

* * * * *